(12) United States Patent
DeAnna

(10) Patent No.: US 7,270,008 B1
(45) Date of Patent: Sep. 18, 2007

(54) INERTIAL TESTING METHOD AND APPARATUS FOR WAFER-SCALE MICROMACHINED DEVICES

(75) Inventor: Russell G. DeAnna, Anniston, AL (US)

(73) Assignee: United States of America as represented by the Secretary of the Army, Washington, DC (US)

( * ) Notice: Subject to any disclaimer, the term of this patent is extended or adjusted under 35 U.S.C. 154(b) by 53 days.

(21) Appl. No.: 10/997,008

(22) Filed: Nov. 26, 2004

(51) Int. Cl.
*G01M 7/02* (2006.01)
*G01M 7/08* (2006.01)
*G01B 7/16* (2006.01)
*G01B 1/00* (2006.01)

(52) U.S. Cl. .......................... 73/663; 73/778
(58) Field of Classification Search ............... 73/12.01, 73/571, 573, 663, 666, 81, 774–779, 756
See application file for complete search history.

(56) References Cited

U.S. PATENT DOCUMENTS

| | | | |
|---|---|---|---|
| 3,187,566 A * | 6/1965 | Coombs | 73/663 |
| 4,603,587 A * | 8/1986 | Kimball et al. | 73/663 |
| 5,014,000 A * | 5/1991 | Schlagheck | 324/754 |
| 5,528,151 A | 6/1996 | Perez | |
| 6,053,034 A * | 4/2000 | Tsui et al. | 73/81 |
| 6,424,165 B1 * | 7/2002 | de Boer et al. | 324/754 |
| 6,817,255 B2 * | 11/2004 | Haque et al. | 73/862.638 |

* cited by examiner

Primary Examiner—Hezron Williams
Assistant Examiner—Rose M. Miller
(74) Attorney, Agent, or Firm—Edward L. Stolarun

(57) ABSTRACT

A method and apparatus for simultaneous fracture and fatigue testing of a semiconductor wafer which includes installing an array of cantilever beams on the wafer, wherein each of the cantilever beams includes a proof mass; mounting the wafer on a base; actuating the base at a predetermined rate of motion causing a displacement of the proof mass; and measuring the displacement. The actuating causes the array to oscillate in a direction perpendicular to the wafer, wherein the displacement of the proof mass is generally perpendicular to a plane of the wafer. Alternatively, the actuating causes the array to rotate around a center of the array, wherein the displacement of the proof mass is generally parallel to a plane of the wafer. The displacement is a function of mechanical stress and strain in the cantilever beams, wherein the mechanical stress and strain causes any of fracture and fatigue of the cantilever beams.

37 Claims, 5 Drawing Sheets

Figure 4(a)

```
┌─────────────────────────────────────────────────┐
│ Installing an array of cantilever beams on a    │
│ wafer, wherein each of the cantilever beams     │──── 40a
│ comprises a proof mass.                         │
└─────────────────────────────────────────────────┘
                      ↓
┌─────────────────────────────────────────────────┐
│ Mounting the wafer on a base.                   │──── 42a
└─────────────────────────────────────────────────┘
                      ↓
┌─────────────────────────────────────────────────┐
│ Actuating the base at a predetermined rate of   │──── 44a
│ motion causing a displacement of the proof mass.│
└─────────────────────────────────────────────────┘
                      ↓
┌─────────────────────────────────────────────────┐
│ Measuring the displacement of the proof mass.   │──── 46a
└─────────────────────────────────────────────────┘
```

Figure 4(b)

```
┌─────────────────────────────────────────────────┐
│ Installing an array of cantilever beams on a    │
│ wafer, wherein each of the cantilever beams     │──── 40b
│ comprises a proof mass.                         │
└─────────────────────────────────────────────────┘
                      ↓
┌─────────────────────────────────────────────────┐
│ Mounting the wafer on a on a shake table.       │──── 42b
└─────────────────────────────────────────────────┘
                      ↓
┌─────────────────────────────────────────────────┐
│ Moving the shake table up and down at a         │
│ prescribed sinusoidal frequency causing a       │──── 44b
│ displacement of the proof mass.                 │
└─────────────────────────────────────────────────┘
                      ↓
┌─────────────────────────────────────────────────┐
│ Measuring the displacement of the proof mass.   │──── 46b
└─────────────────────────────────────────────────┘
```

Figure 4(c)

Installing an array of cantilever beams on a wafer, wherein each of the cantilever beams comprises a proof mass. — 40c Mounting the wafer on a turntable. — 42c Rotating the turntable at a prescribed speed causing a displacement of the proof mass. — 44c Measuring the displacement of the proof mass. — 46c

INERTIAL TESTING METHOD AND APPARATUS FOR WAFER-SCALE MICROMACHINED DEVICES

GOVERNMENT INTEREST

The invention described herein may be manufactured, used, and/or licensed by or for the United States Government.

BACKGROUND OF THE INVENTION

1. Field of the Invention

The invention generally relates to micro electromechanical systems (MEMS), and more particularly to fracture testing, reliability testing, and fatigue testing of MEMS.

2. Description of the Related Art

Micromachined devices are typically tested individually using force probes which measure the strain on cantilever beams or other beam-type devices. This type of individual testing is quite time consuming and requires sophisticated equipment to measure strains and forces. Some wafer-scale fracture tests have been proposed whereby electrostatic forces between fixed and moving pieces are used to move the device to failure. These methods have the potential to test multiple devices in sequence or possibly in parallel (i.e., simultaneously) if the number of data channels is sufficient. For example, U.S. Pat. No. 5,528,151 issued to Perez, the complete disclosure of which, in its entirety, is herein incorporated by reference, teaches thermal fatigue testing using several test strips anchored to a base.

Nonetheless, electrostatic actuation requires knowledge of the electrical-mechanical interface to convert voltage into mechanical displacement. This causes some uncertainty in measurement. Most prior attempts using electrostatic actuation have generally failed to achieve large enough forces to actually fracture a device. Therefore, there remains a need for wafer-scale or batch testing techniques, which achieves greater measurement accuracy and certainty.

SUMMARY OF THE INVENTION

In view of the foregoing, an embodiment of the invention provides a method for simultaneous fracture and fatigue testing of a plurality of micro electromechanical systems on a semiconductor wafer, wherein the method comprises installing an array of cantilever beams on the wafer, wherein each of the cantilever beams comprises a proof mass; mounting the wafer on a base; actuating the base at a predetermined rate of motion causing a displacement of each proof mass; and measuring the displacements as an indication of the condition of said plurality of micro electromechanical systems. In the step of installing, the cantilever beams comprise spring elements, and the array is formed by configuring an inner hub; attaching the cantilever beams to the inner hub; and attaching the proof mass at an end of each of the cantilever beams.

The method further comprises forming an outer hub connecting to the inner hub. In a first embodiment, the actuating causes the array to oscillate in a direction perpendicular to the wafer, wherein the displacement of the proof mass is generally perpendicular to the plane of the wafer. In a second embodiment, the actuating causes the array to rotate around a center of the array, wherein the displacement of the proof mass is generally parallel to the plane of the wafer. Moreover, the displacement is a function of mechanical stress and strain in the cantilever beams, wherein the mechanical stress and strain causes any of fracture and fatigue of the cantilever beams. The method further comprises increasing the rate of motion of the base until any of the cantilever beams or the proof mass structurally fails, or maintaining a constant rate of motion of the base until any of the cantilever beams or the proof mass structurally fails.

According to the first embodiment, the invention provides a method for simultaneous fracture and fatigue testing of a semiconductor wafer, wherein the method comprises installing an array of cantilever beams on the wafer, wherein each of the cantilever beams comprises a proof mass; mounting the wafer on a shake table; moving the shake table up and down at a prescribed sinusoidal frequency and amplitude causing a displacement of the proof mass; and measuring the displacement, wherein the moving causes the array to oscillate in a direction perpendicular to the wafer, wherein the displacement of the proof mass is generally perpendicular to the plane of the wafer, and wherein the displacement is a function of mechanical stress and strain in the cantilever beams, wherein the mechanical stress and strain causes any of fracture and fatigue of the cantilever beams.

According to the second embodiment, the invention provides a method for simultaneous fracture and fatigue testing of a semiconductor wafer, wherein the method comprises installing an array of cantilever beams on the wafer, wherein each of the cantilever beams comprises a proof mass; mounting the wafer on a turntable; rotating the turntable at a prescribed angular velocity causing a displacement of the proof mass; and measuring the displacement, wherein the rotating causes the array to rotate around a center of the array, wherein the displacement of the proof mass is generally parallel to the plane of the wafer, and wherein the displacement is a function of mechanical stress and strain in the cantilever beams, wherein the mechanical stress and strain causes any of fracture and fatigue of the cantilever beams. The method further comprises increasing the rate of motion of the base until any of the cantilever beams or the proof mass structurally fails, or maintaining a constant rate of motion of the base until any of the cantilever beams or the proof mass structurally fails.

Another aspect of the invention provides an apparatus for simultaneous fracture and fatigue testing of a semiconductor wafer, wherein the apparatus comprises a base adapted to hold the wafer; an array of cantilever beams configured on the wafer; a proof mass connected to an end portion of each of the cantilever beams; an actuator configured for actuating the base at a predetermined rate of motion causing displacement of the proof mass; and a gauge configured to the wafer, wherein the gauge is configured for measuring the displacement. Moreover, the cantilever beams comprise spring elements and the array comprises an inner hub connected to the cantilever beams and an outer hub connected to the inner hub.

In a first embodiment, the actuator comprises a shake table configured for oscillating the array in a direction perpendicular to the wafer, wherein the displacement of the proof mass is generally perpendicular to the plane of the wafer. In a second embodiment, the actuator comprises a turntable configured for rotating the array around a center of the array, wherein the displacement of the proof mass is generally parallel to the plane of the wafer. Additionally, the displacement is a function of mechanical stress and strain in the cantilever beams, wherein the mechanical stress and strain causes any of fracture and fatigue of the cantilever beams. Furthermore, in the first embodiment the gauge comprises any of a parallel-plate capacitor and an optical sensor, and in the second embodiment the gauge comprises at least one electrode.

The embodiments of the invention allow a full wafer of MEMS devices to be tested simultaneously. Moreover, an embodiment of the invention uses inertial forces (e.g., either spinning a wafer or shaking a wafer) to achieve the necessary forces to fracture the individual MEMS. With the entire wafer mounted on either a shake table or turntable, the MEMS only undergo an inertial force. Furthermore, the embodiments of the invention provide for batch testing that greatly reduces testing time and cost. Accordingly, embodiments of the invention provide two inertial-testing methods; a wafer mounted on a shake table experiencing sinusoidal oscillations and a wafer mounted on a turntable spinning at an angular rate.

These and other aspects of the embodiments of the invention will be better appreciated and understood when considered in conjunction with the following description and the accompanying drawings. It should be understood, however, that the following descriptions, while indicating preferred embodiments of the invention and numerous specific details thereof, are given by way of illustration and not of limitation. Many changes and modifications may be made within the scope of the embodiments of the invention without departing from the spirit thereof, and the embodiments of the invention include all such modifications.

BRIEF DESCRIPTION OF THE DRAWINGS

The embodiments of the invention will be better understood from the following detailed description with reference to the drawings, in which:

FIG. 4(a) is a flow diagram illustrating preferred method of an embodiment of the invention;

FIG. 4(b) is a flow diagram illustrating a method according to a first embodiment of the invention; and FIG. 4(c) is a flow diagram illustrating a method according to a second embodiment of the invention.

DETAILED DESCRIPTION OF PREFERRED EMBODIMENTS OF THE INVENTION

Figure 1:
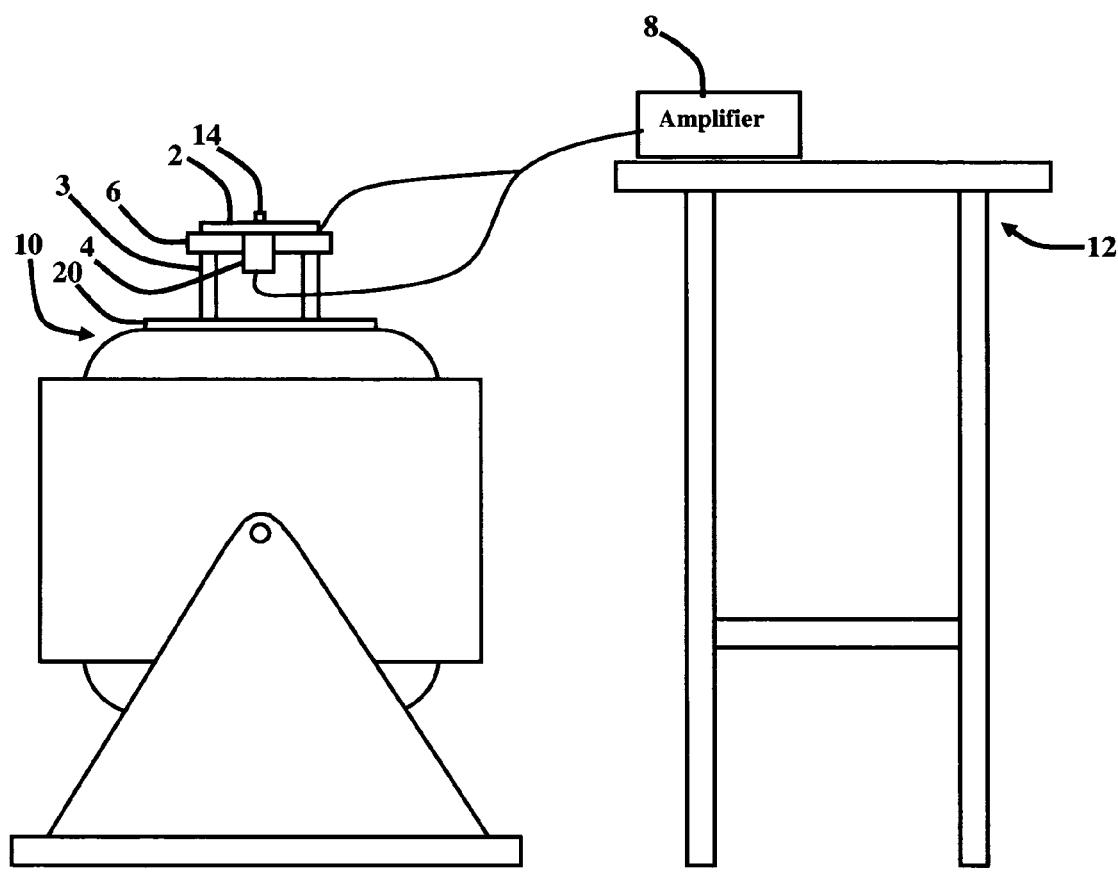
FIG. 1 is a schematic diagram of a testing apparatus according to an embodiment of the invention.
Figure 2A:
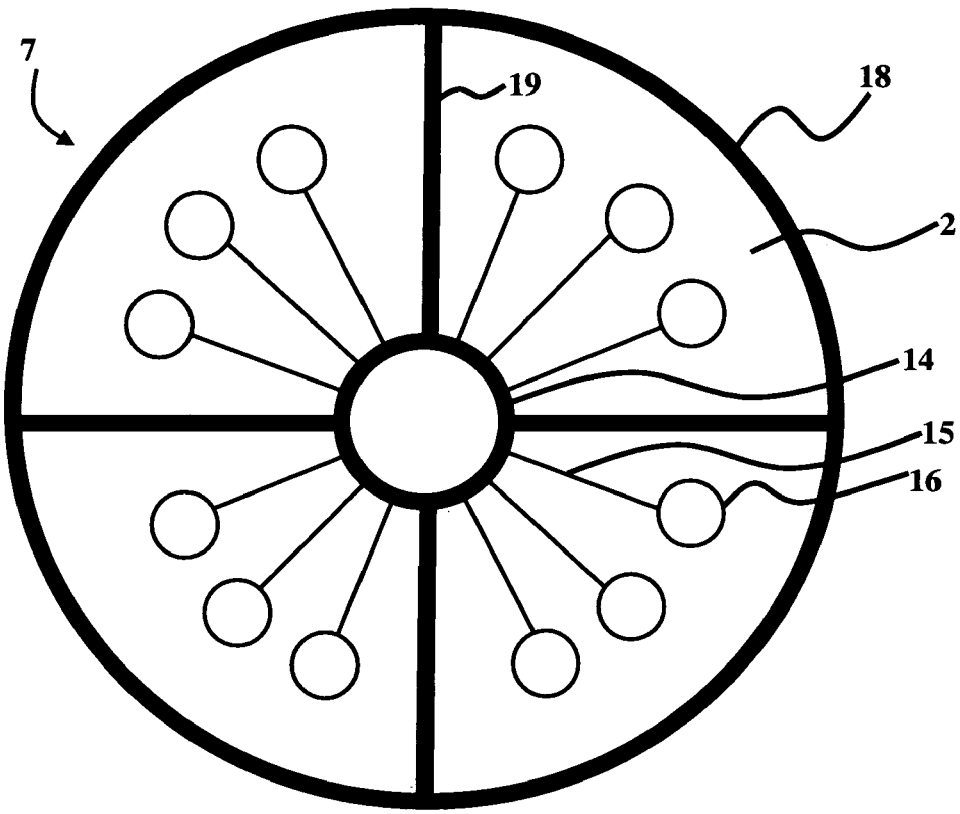
FIG. 2(a) is top view of an apparatus of a wafer with test devices according to an embodiment of the invention.
Figure 2B:
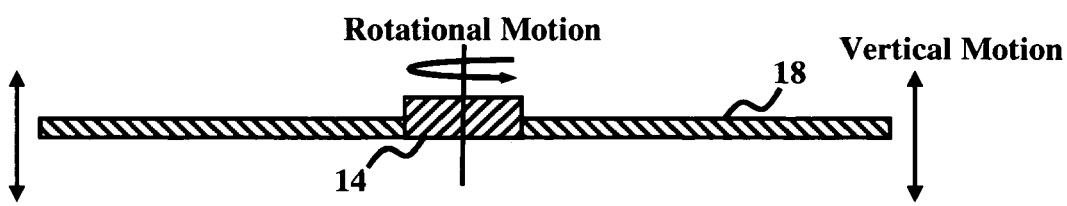
FIG. 2(b) is a side view of the apparatus of FIG. 2(a) according to an embodiment of the invention.
Figure 2C:
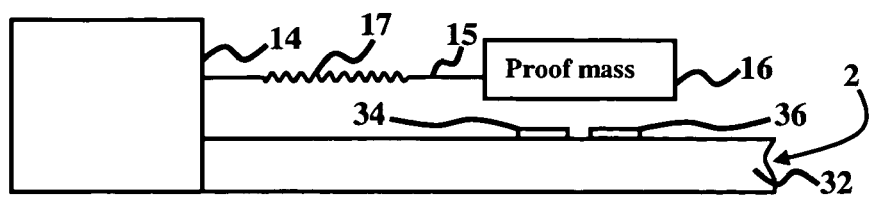
FIG. 2(c) is an alternate side view of the apparatus of FIG. 2(a) according to an embodiment of the invention.
Figure 3A:
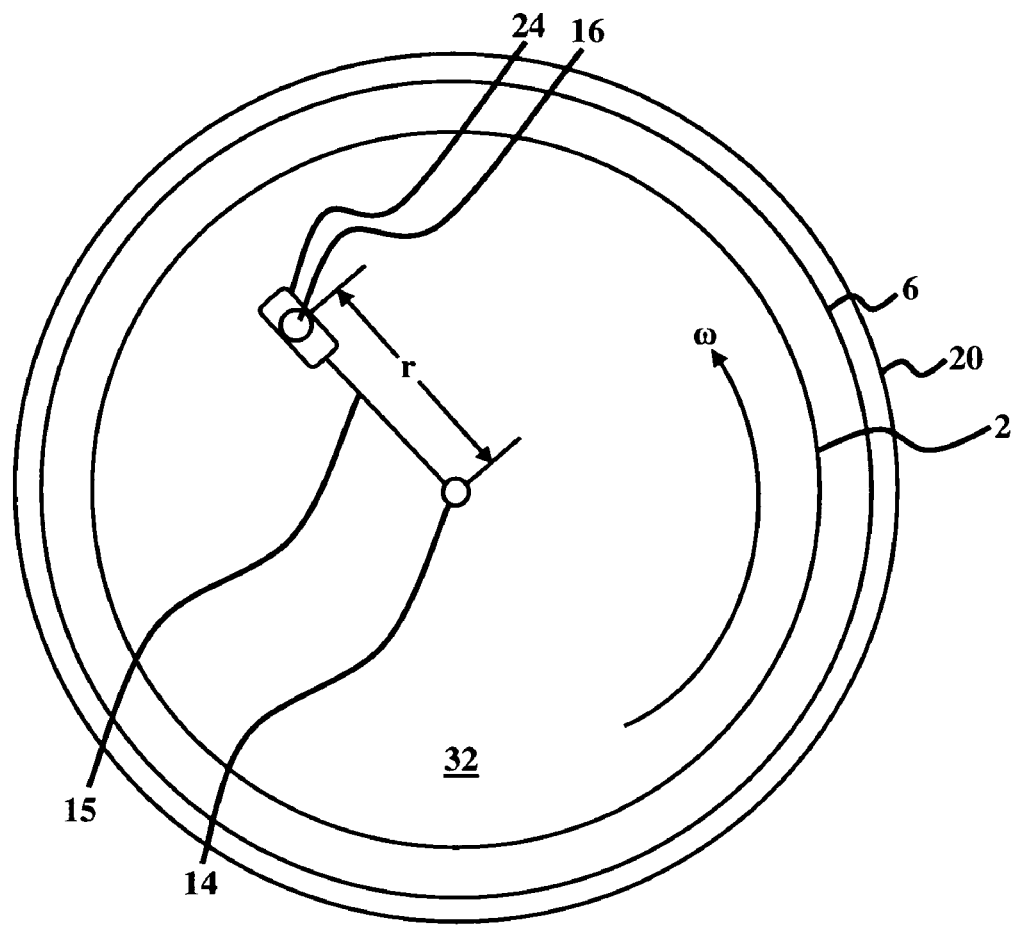
FIG. 3(a) is a top view of an apparatus of a wafer mounted on a turntable according to an embodiment of the invention.
Figure 3B:
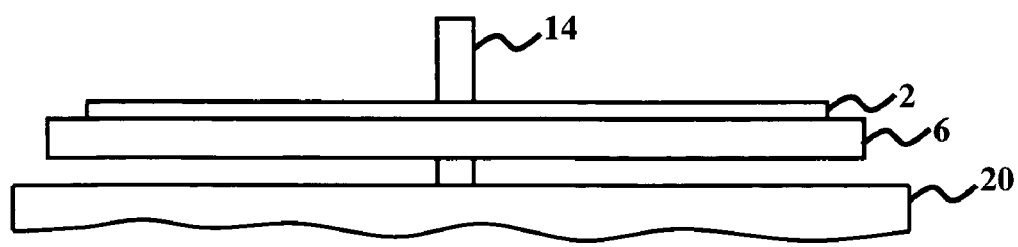
FIG. 3(b) is a side view of the apparatus of FIG. 3(a) according to an embodiment of the invention.

The embodiments of the invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the embodiments of the invention. The examples used herein are intended merely to facilitate an understanding of ways in which the embodiments of the invention may be practiced and to further enable those of skill in the art to practice the embodiments of the invention. Accordingly, the examples should not be construed as limiting the scope of the embodiments of the invention.

As mentioned, there remains a need for a wafer-scale or batch testing technique, which achieves greater measurement accuracy and certainty. Referring now to the drawings, and more particularly to FIGS. 1 through 4(c), there are shown preferred embodiments of the invention.

Embodiments of the invention are illustrated in FIGS. 1 through 3(b), which shows various views of an apparatus for the simultaneous fracture and fatigue testing of a plurality of micro electromechanical systems (not shown) formed on a semiconductor wafer 2. The apparatus depicted in FIG. 1 provides for both a shake table 3 and turntable 20 according to one embodiment. However, those skilled in the art would understand that the apparatus may be configured to include only a shake table 3 in a first alternate embodiment and only a turntable 20 in a second alternate embodiment. The apparatus comprises a base 6 adapted to hold the wafer 2, an array 7 of cantilever beams 15 configured on the wafer 2, a proof mass 16 connected to an end portion of each of the cantilever beams 15, an actuator 10 configured for actuating the base 6 at a predetermined rate of motion thereby causing displacement of the proof mass 16, and a gauge 4 configured to the wafer 2, wherein the gauge 4 is configured for measuring the displacement. In one embodiment, the gauge 4 does not necessarily move with the wafer 2 but may be instead fixed to another structure in the apparatus.

Moreover, the cantilever beams 15 comprise spring elements 17 and the array 7 comprises an inner hub 14 connected to the cantilever beams 15 and an outer hub 18 connected to the inner hub 14 by spokes 19. In a first embodiment, the actuator 10 comprises a shake table 3 configured for oscillating the array 7 in a direction perpendicular to the wafer 2, wherein the displacement of the proof mass 16 is generally perpendicular to the plane of the wafer 2. Furthermore, in the first embodiment the gauge 4 comprises a system of sensors 24 such as a parallel-plate capacitor or optical sensor. Additionally, the gauge 4 may be located either above or below the plane of the wafer 2. In the parallel-plate capacitor embodiment, the gauge 4 could be part of the wafer substrate 32 and could move with the wafer 2, proof masses 16, and cantilever beams 15. Furthermore, the gauge 4 may be attached to an amplifier 8 set on a mount 12 to allow for an amplification of the measurement signals for proper read-out of the results.

In a second embodiment, the actuator 10 comprises a turntable 20 configured for rotating the array 7 about the inner hub 14, wherein the displacement of the proof mass 16 is generally parallel to the plane of the wafer 2. Furthermore, in the second embodiment the gauge 4 comprises at least one electrode 34, 36. Additionally, the displacement is a function of mechanical stress and strain in the cantilever beams 15, wherein the mechanical stress and strain causes any of fracture and fatigue of the cantilever beams 15.

As the shake table 3 moves up and down at a sinusoidal frequency with a given amplitude, the base 6 including the wafer 2 moves with shake table 3. Above the resonant frequency of the combination cantilever beam 15 and proof mass 16, as the shake table 3 and wafer 2 oscillate up and down, the proof mass 16 on the end of each cantilever beam 15 remains approximately fixed in space. This relative motion between the proof mass 16 and wafer 2 creates mechanical strain in the cantilever beam 15. At a sufficiently high frequency and/or amplitude (the amount of which depends on the geometry and material of the cantilever beam 15 and proof mass 16), this strain will cause the cantilever beam 15 to fail and break.

The motion of the proof mass 16 is perpendicular to the plane of wafer 2 when the cantilever beam 15 and proof mass 16 undergoes oscillation. A sufficient volume of the substrate 32 of the wafer 2 beneath the proof mass 16 is etched or removed to allow for the oscillation of proof mass displacement. As mentioned, the gauge 4 is used for measuring displacement of the proof mass 16, wherein the gauge 4 may be configured as a system of sensors 24 embodied as a parallel-plate capacitor configured around the perimeter of the proof mass 16, or alternatively embodied as an optical sensor. As such, a corresponding pattern of capacitor plates (shown as sensor 24 in FIG. 3(a)) on the fixed substrate 32 could be used to measure the capacitance change as the proof mass 16 moves out of the plane of wafer 2. The sensors 24 also detect failure of the cantilever beam 15 because the capacitance would change if the proof mass 16 was removed due to failure of the cantilever beam 15.

As the turntable 20 spins at an angular rotation rate, ω, the centripetal acceleration creates a radially oriented inertial force which acts on cantilever beam 15 and proof mass 16. This radial inertial force causes the proof mass 16 to move outward and creates a stress and corresponding strain on cantilever beam 15. At a sufficiently high angular velocity, the centripetal force on cantilever beam 15 and proof mass 16 causes the cantilever beam 15 to fail and break.

Because displacement of the proof mass 16 is parallel to the surface of wafer 2, the displacement and failure of the proof mass 16 can be detected by electrostatic measurements of the capacitance between the moving proof mass 16 and fixed electrodes 34, 36 positioned underneath the proof mass 16 and attached to the substrate 32 of the wafer 2. The electrodes 34, 36 could comprise aluminum or another suitable metallic material and may be embodied as electrode plates. In an alternate embodiment, the proof mass 16 could comprise p+ or n-type doped materials to serve as the second electrode for measurement purposes. The two electrodes 34, 36 act like a parallel-plate capacitor in this embodiment. As such, the capacitance change between the two electrodes 34, 36 would increase with an increasing angular rotation rate, ω. This change can then be related to the displacement and strain of the cantilever beam 15 and corresponding proof mass 16. Alternatively, the electrodes 34, 36 positioned underneath the wafer 2 could be fixed to the shake table 3 and turntable 20. In this embodiment, the electrodes 34, 36 measure the capacitance between the electrodes 34, 36 and each of the individual proof masses 16 as the proof masses 16 rotate above providing an intermittent measurement in time.

The inertial force caused by a sinusoidal oscillation of the shake table 3 is given by the equation:

$$F = ma = m\omega_o^2 A \cos(\omega_o t)$$

where m is the mass (kg) of the proof mass, $\omega_o$ is the oscillation frequency (rad/sec), A is the amplitude of the shake table oscillation, and t is time (sec). Below the resonant frequency of the combination proof mass 16 and cantilever beam 15, the proof mass 16 moves with the shake table 3 and no relative motion or strain in the cantilever beam 15 is created. At resonance, the proof mass 16 moves with maximum amplitude and may actually move more than the shake table 3. Well above resonance, where the apparatus provided by an embodiment of the invention would likely operate, the proof mass 16 generally does not move in space as the shake table 3 moves up and down.

The resonant frequency, $\omega_r$, of a spring-mass system, such as the cantilever beam 15 and proof mass 16 combination is given by:

$$\omega_r = \sqrt{\frac{k}{m}}$$

where the cantilever beam stiffness is given by k and the mass of the proof mass 16 is given by m. The stiffness of the cantilever beam 15 may be different for each cantilever beam 15 on the wafer 2. Also, the mass, m, of the proof mass 16 may be different for each proof mass 16 on the wafer 2. Although the mass and stiffness of each cantilever beam 15 and proof mass 16 may be different, in this case, all of the proof masses 16 on the same wafer 2 will experience the same acceleration.

The inertial force caused by rotation of the turntable 20 is given by:

$$F = m\omega^2 r$$

where r is the radial location of the proof mass 16 with respect to the axis of rotation of the wafer 2 and ω is the angular rotation rate. This centripetal acceleration force will push the proof mass 16 outward and create stress in the cantilever beam 15. In this case, the acceleration experienced by any proof mass 16 is proportional to its distance (radial location), r, from the axis of rotation. Hence, only those proof masses 16 at the same radial location will experience the same acceleration. The geometry of the individual array 7 of cantilever beams 15 and proof masses 16 is not critical, as various geometries may be used in accordance with the embodiments of the invention. As such, each cantilever beam 15 may have one or more proof masses 16 and may be configured in any type of geometry, wherein the configuration of the geometry is a matter of choice for the individual designer.

The flowcharts of FIGS. 4(a) through 4(c) include descriptions which refer to components provided in FIGS. 1 through 3(b). The flowchart of FIG. 4(a) illustrates a general method for simultaneous fracture and fatigue testing of a semiconductor wafer 2, wherein the method comprises installing (40a) an array 7 of cantilever beams 15 on the wafer 2, wherein each of the cantilever beams 15 comprises a proof mass 16. The next steps involve mounting (42a) the wafer 2 on a base 6 and actuating (44a) the base 6 at a predetermined rate of motion causing a displacement of the proof mass 16. Finally, the method involves measuring (46a) the displacement of the proof mass 16. In the step of installing (40a), the cantilever beams 15 comprise spring elements 17, and the array 7 is formed by configuring an inner hub 14, attaching the cantilever beams 15 to the inner hub 14, and attaching the proof mass 16 at an end of each of the cantilever beams 15. The method further comprises forming an outer hub 18 connecting to the inner hub 14 by spokes 19.

In a first embodiment, the actuating (44a) causes the array 7 to oscillate in a direction perpendicular to the wafer 2, wherein the displacement of the proof mass 16 is generally perpendicular to the plane of the wafer 2. In a second embodiment, the actuating (44a) causes the array 7 to rotate around a center of the array 7, wherein the displacement of the proof mass 16 is generally parallel to the plane of the wafer 2. Moreover, the displacement is a function of mechanical stress and strain in the cantilever beams 15, wherein the mechanical stress and strain causes any of fracture and fatigue of the cantilever beams 15. In an alternate embodiment, the method provides for increasing the rate of motion of the base 6 until the proof mass 16 or cantilever beam 15 fails, wherein failure is defined as complete structural fracture or excess displacement of the proof mass 16 or cantilever beam 15.

FIG. 4(b) illustrates a flowchart of the first embodiment for simultaneous fracture and fatigue testing of a semiconductor wafer 2, wherein the method of the first embodiment comprises installing (40b) an array 7 of cantilever beams 15 on the wafer 2, wherein each of the cantilever beams 15 comprises a proof mass 16. The next steps involve mounting (42b) the wafer 2 on a shake table 3 and moving (44b) the shake table 3 up and down at a prescribed sinusoidal frequency and amplitude causing a displacement of the proof mass 16. Finally, the method involves measuring (46b) the displacement of the proof mass 16, wherein the moving (44b) causes the array 7 to oscillate in a direction perpendicular to the wafer 2, wherein the displacement of the proof mass 16 is generally perpendicular to the plane of the wafer 2, and wherein the displacement is a function of mechanical stress and strain in the cantilever beams 15, wherein the mechanical stress and strain causes any of fracture and fatigue of the cantilever beams 15.

FIG. 4(c) illustrates a flowchart of the second embodiment for simultaneous fracture and fatigue testing of a semiconductor wafer 2, wherein the method of the second embodiment comprises installing (40c) an array 7 of cantilever beams 15 on the wafer 2, wherein each of the cantilever beams 15 comprises a proof mass 16. The next steps involve mounting (42c) the wafer 2 on a turntable 20 and rotating (44c) the turntable 20 at a prescribed velocity causing a displacement of the proof mass 16. The final step involves measuring (46c) the displacement of the proof mass 16, wherein the rotating (44c) causes the array to rotate around a center of the array 7, wherein the displacement of the proof mass 16 is generally parallel to the plane of the wafer 2, and wherein the displacement is a function of mechanical stress and strain in the cantilever beams 15, wherein the mechanical stress and strain causes any of fracture and fatigue of the cantilever beams 15. Alternatively, the angular velocity of the base 6 may be increased until the cantilever beams 15 or proof mass 16 structurally fails by fracture or fatigue. As a further alternative, the angular velocity of the base 6 may be held constant until the cantilever beams 15 or proof mass 16 structurally fails by creep fracture or fatigue.

General applications utilizing the embodiments of the invention allow for a full wafer of proof masses 16, such as MEMS devices to be tested simultaneously. Moreover, an embodiment of the invention can be applied to use inertial forces (e.g., either spinning a wafer 2 or shaking a wafer 2) to achieve the necessary forces to fracture the individual MEMS devices. With the entire wafer 2 mounted on either a shake table 3 or turntable 20, the MEMS devices only undergoes an inertial force. Furthermore, the embodiments of the invention provide for batch testing that greatly reduces testing time and cost. Accordingly, embodiments of the invention provide two inertial-testing methods; a wafer 2 mounted on a shake table 3 experiencing sinusoidal oscillations and a wafer 2 mounted on a turntable 20 spinning at an angular rate, (o.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the invention has been described in terms of preferred embodiments, those skilled in the art will recognize that the embodiments of the invention can be practiced with modification within the spirit and scope of the appended claims.

What is claimed is:

1. A method for simultaneous fracture and fatigue testing of a plurality of micro electromechanical systems on a semiconductor wafer, said method comprising:
    installing an array of cantilever beams on said wafer, wherein each of said cantilever beams comprises a proof mass;
    mounting said wafer on a base;
    actuating said base at a predetermined rate of motion causing a displacement of each said proof mass; and
    measuring said displacements as an indication of the condition of said plurality of micro electromechanical systems.

2. The method of claim 1, wherein in said installing, said cantilever beams comprise spring elements.

3. The method of claim 1, wherein in said installing, said array is formed by:
    configuring an inner hub;
    attaching said cantilever beams to said inner hub; and
    attaching said proof mass at an end of each of said cantilever beams.

4. The method of claim 3, further comprising forming an outer hub connecting to said inner hub.

5. The method of claim 1, wherein said actuating causes said array to oscillate in a direction perpendicular to said wafer.

6. The method of claim 1, wherein said actuating causes said array to rotate around a center of said array.

7. The method of claim 1, wherein said displacement of said proof mass is generally perpendicular to a plane of said wafer.

8. The method of claim 1, wherein said displacement of said proof mass is generally parallel to a plane of said wafer.

9. The method of claim 1, wherein said displacement is a function of mechanical stress and strain in said cantilever beams, wherein said mechanical stress and strain causes any of fracture and fatigue of said cantilever beams.

10. The method of claim 1, further comprising increasing said rate of motion of said base until any of said cantilever beams or said proof mass structurally fails.

11. The method of claim 1, further comprising maintaining a constant rate of motion of said base until any of said cantilever beams or said proof mass structurally fails.

12. A method for simultaneous fracture and fatigue testing of a plurality of micro electromechanical systems on a semiconductor wafer, said method comprising:
    installing an array of cantilever beams on said wafer, wherein each of said cantilever beams comprises a proof mass;
    mounting said wafer on a shake table;

moving said shake table up and down at a prescribed sinusoidal frequency and amplitude causing a displacement of each said proof mass; and measuring said displacements as an indication of the condition of said plurality of micro electromechanical systems.

13. The method of claim 12, wherein in said installing, said cantilever beams comprise spring elements.

14. The method of claim 12, wherein in said installing, said array is formed by:
configuring an inner hub;
attaching said cantilever beams to said inner hub; and
attaching a proof mass at an end of each of said cantilever beams.

15. The method of claim 14, further comprising forming an outer hub connecting to said inner hub.

16. The method of claim 12, wherein said moving causes said array to oscillate in a direction perpendicular to said wafer.

17. The method of claim 12, wherein said displacement of said proof mass is generally perpendicular to a plane of said wafer.

18. The method of claim 12, wherein said displacement is a function of mechanical stress and strain in said cantilever beams, wherein said mechanical stress and strain causes any of fracture and fatigue of said cantilever beams.

19. A method for simultaneous fracture and fatigue testing of a plurality of micro electromechanical systems on a semiconductor wafer, said method comprising:
installing an array of cantilever beams on said wafer, wherein each of said cantilever beams comprises a proof mass;
mounting said wafer on a turntable;
rotating said turntable at a prescribed velocity causing a displacement of each said proof mass; and
measuring said displacements as an indication of the condition of said plurality of micro electromechanical systems.

20. The method of claim 19, wherein in said installing, said cantilever beams comprise spring elements.

21. The method of claim 19, wherein in said installing, said array is formed by:
configuring an inner hub;
attaching said cantilever beams to said inner hub; and
attaching a proof mass at an end of each of said cantilever beams.

22. The method of claim 21, further comprising forming an outer hub connecting to said inner hub.

23. The method of claim 19, wherein said rotating causes said array to rotate around a center of said array.

24. The method of claim 19, wherein said displacement of said proof mass is generally parallel to a plane of said wafer.

25. The method of claim 19, wherein said displacement is a function of mechanical stress and strain in said cantilever beams, wherein said mechanical stress and strain causes any of fracture and fatigue of said cantilever beams.

26. The method of claim 19, further comprising increasing said sinusoidal frequency of said turntable until any of said cantilever beams or said proof mass structurally fails.

27. The method of claim 19, further comprising maintaining a constant sinusoidal frequency of said turntable until any of said cantilever beams or said proof mass structurally fails.

28. An apparatus for simultaneous fracture and fatigue testing of a plurality of micro electromechanical systems on a semiconductor wafer, said apparatus comprising:
a base for holding said wafer;
an array of cantilever beams configured on said wafer;
a proof mass connected to an end portion of each of said cantilever beams;
an actuator configured for actuating said base at a predetermined rate of motion causing displacement of each said proof mass; and
a gauge means proximate said wafer for monitoring the displacement of each said proof mass;
wherein the monitored displacements provide an indication of the mechanical stress encountered by said cantilever beams as an indication of the condition of said plurality of micro electromechanical systems.

29. The apparatus of claim 28, wherein said cantilever beams comprise spring elements.

30. The apparatus of claim 28, wherein said array comprises:
an inner hub connected to said cantilever beams; and
an outer hub connected to said inner hub.

31. The apparatus of claim 28, wherein said actuator comprises a shake table configured for oscillating said array in a direction perpendicular to said wafer.

32. The apparatus of claim 28, wherein said actuator comprises a turntable configured for rotating said array around a center of said array.

33. The apparatus of claim 28, wherein said displacement of said proof mass is generally perpendicular to a plane of said wafer.

34. The apparatus of claim 28, wherein said displacement of said proof mass is generally parallel to a plane of said wafer.

35. The apparatus of claim 28, wherein said displacement is a function of mechanical stress and strain in said cantilever beams, wherein said mechanical stress and strain causes any of fracture and fatigue of said cantilever beams.

36. The apparatus of claim 28, wherein said gauge comprises any of a parallel-plate capacitor and an optical sensor.

37. The apparatus of claim 28, wherein said gauge comprises at least one electrode.

* * * * *